US011612583B2

(12) United States Patent
Dagda et al.

(10) Patent No.: US 11,612,583 B2
(45) Date of Patent: Mar. 28, 2023

(54) DISEASE MODIFYING METHODS FOR TREATING NEURODEGENERATIVE DISEASES USING NOOTROPIC AGENTS

(71) Applicant: Nevada Research & Innovation Corporation, Reno, NV (US)

(72) Inventors: Raul Y. Dagda, Reno, NV (US); Ruben K. Dagda, Reno, NV (US)

(73) Assignee: Nevada Research & Innovation Corporation, Reno, NV (US)

( * ) Notice: Subject to any disclaimer, the term of this patent is extended or adjusted under 35 U.S.C. 154(b) by 180 days.

(21) Appl. No.: 17/055,349

(22) PCT Filed: Jun. 20, 2019

(86) PCT No.: PCT/US2019/038239
§ 371 (c)(1),
(2) Date: Nov. 13, 2020

(87) PCT Pub. No.: WO2019/246398
PCT Pub. Date: Dec. 26, 2019

(65) Prior Publication Data
US 2021/0220322 A1     Jul. 22, 2021

Related U.S. Application Data

(60) Provisional application No. 62/688,189, filed on Jun. 21, 2018.

(51) Int. Cl.
*A61K 31/352* (2006.01)
*A61K 9/00* (2006.01)
*A61K 9/12* (2006.01)
*A61K 31/4015* (2006.01)
*A61K 45/06* (2006.01)

(52) U.S. Cl.
CPC .......... *A61K 31/352* (2013.01); *A61K 9/0043* (2013.01); *A61K 9/12* (2013.01); *A61K 31/4015* (2013.01); *A61K 45/06* (2013.01)

(58) Field of Classification Search
CPC .............. A61K 31/352; A61K 31/4015; A61K 31/428; A61P 25/16; A61P 25/28
See application file for complete search history.

(56) References Cited

U.S. PATENT DOCUMENTS

| 6,514,999 B1 * | 2/2003 | Saiger | A61P 25/16 |
| | | | 514/354 |
| 2005/0009847 A1 | 1/2005 | Bertilsson et al. | |
| 2008/0044390 A1 * | 2/2008 | Jin | A61P 25/28 |
| | | | 514/35 |
| 2009/0176740 A1 | 7/2009 | Phillips | |

FOREIGN PATENT DOCUMENTS

| EP | 1583541 A2 | 10/2005 |
| WO | 2013134047 A2 | 9/2013 |
| WO | 2016011270 A2 | 1/2016 |

OTHER PUBLICATIONS

International Search Report and Written Opinion, PCT/US2019/038239, dated Oct. 17, 2019.
Morinobu, et al., "Stimulation of adenylyl cyclase and induction of brain-derived neurotrophic factor and TrkB mRNA by NKH477, a novel and potent forskolin derivative", Journal of Neurochemistry, 1999, vol. 72, No. 5, pp. 2198-2205.
Ostrovskaya, et al., "Neuroprotective effect of novel cognitive enhancer noopept on AD-related cellular model involves the attenuation of apoptosis and tau hyperphosphorylation", Journal of Biomedical Science, 2014, vol. 21, No. 74, pp. 1-9.
Extended EP Search Report and Written Opinion, European Patent Application No. 19 823 342.1, dated Mar. 24, 2022.
Jia, et al., "Neuroprotective and Nootropic Drug Noopept Rescues [alpha]-Synuclein Amyloid Cytotoxicity", Journal of Molecular Biology, vol. 414, No. 5, Dec. 1, 2011 (Dec. 1, 2011), pp. 699-712, XP055900974, United Kingdom, ISSN: 0022-2836, DOI:10.1016/j.jmb.2011.09.044.

* cited by examiner

*Primary Examiner* — Sahar Javanmard
(74) *Attorney, Agent, or Firm* — Saul Ewing LLP; Kathryn Doyle

(57) ABSTRACT

The present invention relates to the discovery that Forskolin can be used to treat Parkinson's disease (PD) in subjects in need thereof. In certain embodiments, the invention provides a method of treating PD, wherein a therapeutically effective amount of Forskolin is administered to a subject via intranasal or intrapulmonary routes. In other embodiments, the subject is further administered a therapeutically effective amount of Noopept. In yet other embodiments, the method reverses damage to the subject's brain caused by PD and promotes growth of new neurons.

28 Claims, 11 Drawing Sheets

DISEASE MODIFYING METHODS FOR TREATING NEURODEGENERATIVE DISEASES USING NOOTROPIC AGENTS

CROSS-REFERENCE TO RELATED APPLICATIONS

The present application is a 35 U.S.C. § 371 national phase application from, and claiming priority to, International Application No. PCT/US2019/038239, filed Jun. 20, 2019, which claims priority under 35 U.S.C. § 119(e) to U.S. Provisional Patent Application No. 62/688,189, filed Jun. 21, 2018, all of which are incorporated herein by reference in their entireties.

STATEMENT REGARDING FEDERALLY SPONSORED RESEARCH OR DEVELOPMENT

This invention was made with government support under grant number GM103554 and NS105783 awarded by the National Institutes of Health/National Institute of General Medical Sciences. The government has certain rights in the invention.

BACKGROUND OF THE INVENTION

Parkinson's disease (PD) is a chronic, neurodegenerative disease that affects up to 1% of the world population. PD is a multifactorial disease with a range of reported causes and factors including aging (>65 years), genetic mutations, and environmental factors (mitochondria-targeted toxins and intoxicants). While 90% of PD cases are idiopathic, approximately 10% of PD cases are associated with gene mutations in 18 different genes that are critical for modulating protein quality control, mitochondrial and lysosomal function, cytoskeletal dynamics, antioxidant responses, and protein kinase signaling. PD is pathologically characterized by the progressive loss of substantia nigra dopamine neurons in the midbrain, which leads to irreversible, impaired motor function in patients including bradykinesia, lack of initiation of movement, and loss of balance in advanced stages of PD. Clinical symptoms of PD manifest when approximately more than 90% of midbrain dopamine neurons are lost in the PD patient.

In addition to targeting the midbrain and striatum, a significant loss of cortical mass, due to loss of dendrites, has been observed in individuals with late stage PD. A decrease in the utilization of energy derived from glucose, and other essential nutrients, in the brain contributes to neuropathology in PD. Importantly, cortical and midbrain dopamine neurons experience a excessive levels of oxidative stress leading to cortical syncytium, and the accumulation of large intracellular protein aggregates termed Lewy bodies. The loss of cortical neurons in PD contributes to the onset of dementia in at least 50% of PD cases and it is comorbid with psychiatric diseases including major clinical depression.

Medical-related costs of PD are currently estimated to be at $14.4 billion per year in the United States alone. The lack of therapies that can delay or reverse neurodegeneration in PD, along with the continued rise in PD cases per year, underscores the need to develop new therapies that can reverse neurodegeneration and induce neurogenesis to repopulate the lost neurons in the midbrain and cortex. Current therapies only alleviate PD clinical symptoms without reversing neurodegeneration of midbrain dopamine and cortical neurons. Oral or intravenous administration of Levodopa (L-DOPA) in patients successfully elevates the bioavailability of dopamine in the midbrain, which partially restores dopamine neurotransmission. Unfortunately, PD patients become resistant to L-DOPA treatment with time leading to the onset of additional clinical symptoms (e.g. inability to swallow). Monoamine oxidase B inhibitors (e.g. selegiline and rasagiline) and dopamine receptor 2 agonists (e.g. Bromocriptine) can help alleviate clinical symptoms in PD patients resistant to L-DOPA by enhancing the availability of dopamine. Unfortunately, these treatments are not disease-modifying and only provide a modest relief of symptoms.

Therefore, there remains a need in the art for novel, disease-modifying methods and formulations for the treatment of Parkinson's disease in a subject in need thereof. In certain embodiments, the methods are disease-modifying therapies that can reverse the loss of dopamine and cortical neurons, and restore dopamine levels in the brain.

BRIEF SUMMARY OF THE INVENTION

In one aspect, the invention provides a method of treating at least one neurodegenerative disease or disorder in a subject in need thereof. In another aspect, the invention provides a kit for treating a neurodegenerative disease or disorder in a subject in need thereof.

In certain embodiments, the method comprises administering to the subject a therapeutically effective amount of at least one Forskolin analogue, or a salt, isomer, prodrug or solvate thereof, wherein the at least one Forskolin analogue is selected from the group consisting of:

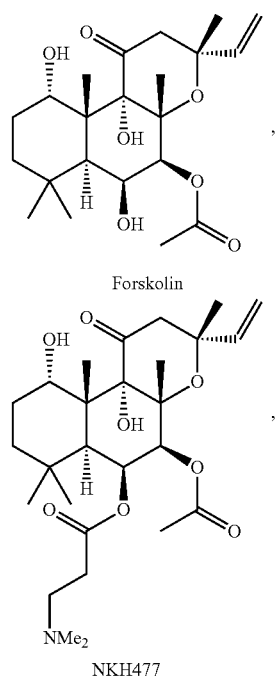

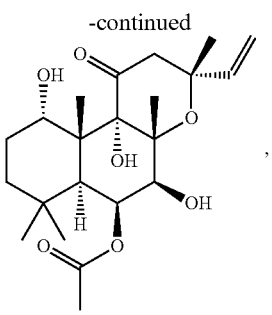

iso-Forskolin

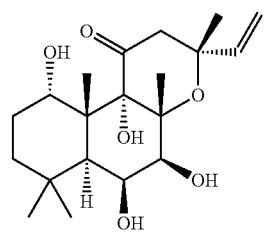

deacetyl-Forskolin, and any deoxygenated derivatives thereof.

In certain embodiments, the at least one neurodegenerative disease or disorder is selected from the group consisting of Parkinson's disease (PD), Lewy Body Dementia (LBD), Alzheimer's disease, and frontotemporal dementia.

In certain embodiments, the therapeutically effective amount of the at least one Forskolin analogue, or a salt, prodrug or solvate thereof is administered to the subject intranasally.

In certain embodiments, the therapeutically effective amount of the at least one Forskolin analogue, or a salt, prodrug or solvate thereof, is administered to the subject at least once per day, at least once every two days, at least once every three days, at least once per week or any frequencies and intervals there between.

In certain embodiments, the therapeutically effective amount of the at least one Forskolin analogue, or a salt, prodrug or solvate thereof, is administered to the subject intranasally at least once per day to each nostril.

In certain embodiments, the therapeutically effective amount of the at least one Forskolin analogue, or a salt, prodrug or solvate thereof, is about 0.1 mg/kg to about 10 mg/kg (Forskolin weight/subject body weight).

In certain embodiments, the therapeutically effective amount of the at least one Forskolin analogue, or a salt, prodrug or solvate thereof, is about 0.1 mg to about 100 mg.

In certain embodiments, the therapeutically effective amount of the at least one Forskolin analogue, or a salt, prodrug or solvate thereof, is administered as part of a pharmaceutical composition further comprising at least one pharmaceutically acceptable carrier.

In certain embodiments, the therapeutically effective amount of the at least one Forskolin analogue, or a salt, prodrug or solvate thereof, is administered as part of an aerosolizable pharmaceutical composition.

In certain embodiments, the pharmaceutical composition comprises at least one Forskolin analogue, or a salt, prodrug or solvate thereof, such that the total Forskolin analogue concentration is about 0.1 µM to about 20 µM In certain embodiments, the pharmaceutical composition comprises at least one pharmaceutically acceptable solvent selected from the group consisting of a buffered aqueous solution, a buffered saline solution, ethanol, water, propylene glycol, polyethylene glycol (PEG), glycofurol, dimethylsulfoxide (DMSO) and (4-(2-hydroxyethyl)-1-piperazineethanesulfonic acid) (HEPES). In certain embodiments, the pharmaceutical composition further comprises at least one additional component selected from the group consisting of a pharmaceutically acceptable salt, an emulsifying agent, a flavorant, a scenting agent, a stabilizer, a preservative and a chelating agent. In certain embodiments, the pharmaceutical composition is a buffered pharmaceutical composition.

In certain embodiments, the subject is further administered a therapeutically effective amount of at least one Noopept analogue, or a salt, prodrug or solvate thereof. In certain embodiments, the at least one Noopept analogue is a compound selected from the group consisting of Noopept, piracetam, oxyracetam, aniracetam, and pramiracetam.

In certain embodiments, the therapeutically effective amount of the at least one Noopept analogue, or a salt, prodrug or solvate thereof, is administered to the subject orally. In certain embodiments, the therapeutically effective amount of the at least one Noopept analogue or a salt, prodrug or solvate thereof is about 0.01 mg/kg to about 5 mg/kg (Noopept analogue weight/subject body weight). In certain embodiments, the therapeutically effective amount of the at least one Noopept analogue, or a salt, prodrug or solvate thereof is about 5 mg to about 50 mg.

In certain embodiments, the therapeutically effective amount of the at least one Noopept analogue, or a salt, prodrug or solvate thereof, is administered to the subject after the at least one Forskolin analogue or a salt, prodrug or solvate thereof is administered to the subject.

In certain embodiments, the at least one Forskolin analogue, or a salt, prodrug or solvate thereof, is administered intranasally for about 5 days to about 14 days before beginning administration of the therapeutically effective amount of the at least one Noopept analogue, or a salt, prodrug or solvate thereof.

In certain embodiments, the method further comprises administering to the subject at least one additional agent for the treatment of Parkinson's disease. In certain embodiments, the at least one additional agent for the treatment of Parkinson's disease is selected from the group consisting of cyclic AMP, levodopa (L-dopa), cabidopa, ropinirole, pramipexole, rotigotine, amantadine, trihexyphenidyl, benztropine, selegiline, rasagiline, tolcapone, entacapone, pergolide, ropinirole, phenylzine, tranylcypromine, isocarboxazid, entacapone, and artane.

In certain embodiments, the method promotes dendritogenesis and/or neurogenesis in the brain of the subject. In certain embodiments, the method reverses the loss of coordination and balance in the subject. In certain embodiments, the method reverses the loss of muscle strength in the subject. In certain embodiments, the method reverses the loss in oxidative phosphorylation in the midbrain of the subject. In certain embodiments, the method reverses the loss of substantia nigra dopamine neurons in the midbrain of the subject.

In certain embodiments, the subject is a mammal. In certain embodiments, the subject is a human.

In certain embodiments, the kit comprises a pharmaceutical composition comprising at least one Forskolin analogue, or a salt, prodrug or solvate thereof, a pharmaceutical composition comprising the at least one Noopept analogue, or a salt, prodrug or solvate thereof, and instructional materials detailing methods of treating a neurodegenerative disease or disorder using the pharmaceutical compositions of the kit.

In certain embodiments, the kit further comprises an applicator for the intranasal administration of the pharmaceutical composition comprising at least one Forskolin analogue or a salt, prodrug or solvate thereof, to a subject.

BRIEF DESCRIPTION OF THE DRAWINGS

For the purpose of illustrating the invention, depicted in the drawings are certain embodiments of the invention. However, the invention is not limited to the precise arrangements and instrumentalities of the embodiments depicted in the drawings.

DETAILED DESCRIPTION OF THE INVENTION

Figure 1:
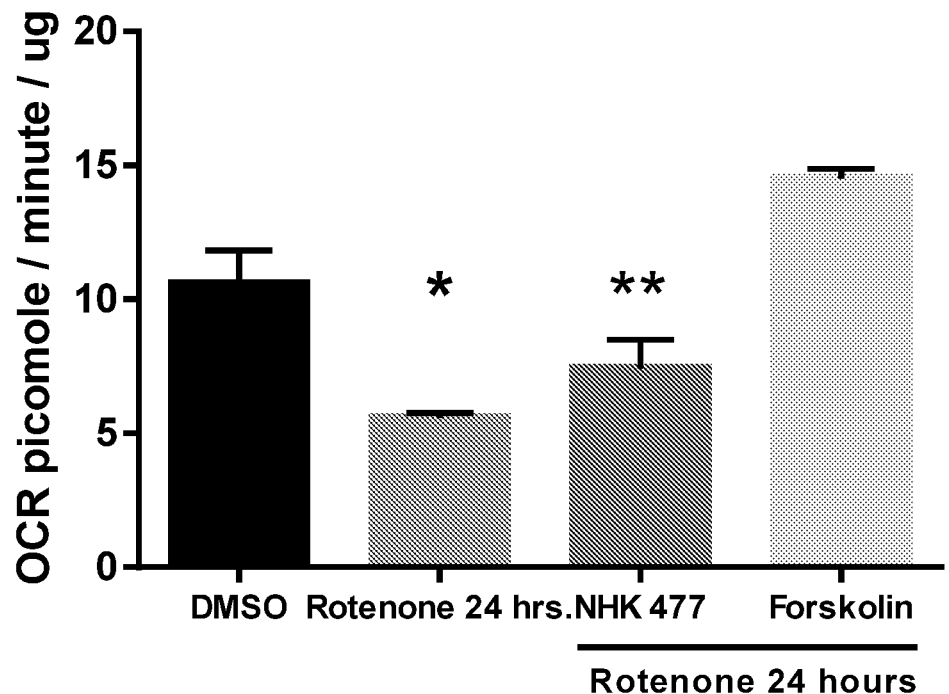
FIG. 1 is a graph showing that Forskolin significantly restored baseline mitochondrial respiration in primary cortical neurons treated with rotenone, an in vitro chemical model of PD.

The present invention relates to the discovery that Forskolin can be used to treat Parkinson's disease (PD) in subjects in need thereof. In certain embodiments, the invention provides a method of treating PD wherein a therapeutically effective amount of Forskolin is administered to a subject intranasally. In other embodiments, the subject is further administered a therapeutically effective amount of Noopept. In yet other embodiments, the method reverses damage to the subject's brain caused by PD and promotes growth of new neurons.

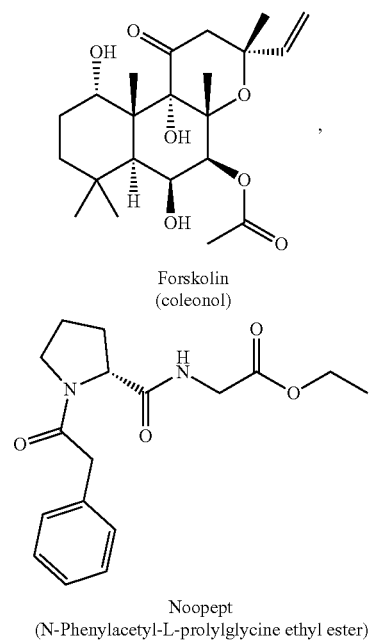

Forskolin
(coleonol)

Noopept
(N-Phenylacetyl-L-prolylglycine ethyl ester)

Methods

In one aspect, the invention provides a method for treating at least one neurodegenerative disease or disorder, including Parkinson's disease and related neurodegenerative diseases and disorders, in a subject in need thereof. In certain embodiments, the at least one neurodegenerative disease or disorder is one that affects the cortex of the subject. In other embodiments, the at least one neurodegenerative disease or disorder causes a decrease in neuronal metabolism. In yet other embodiments, the at least one disease or disorder is selected from the group consisting of Parkinson's disease (PD), Lewy Body Dementia (LBD), Alzheimer's disease, and frontotemporal dementia (Pick's disease). In yet other embodiments, the at least one disease or disorder is a form of dementia, including, but not necessarily limited to Lewy Body Dementia (LBD), Parkinson's disease dementia, Parkinson's disease comorbid with Alzheimer's disease dementia, senile dementia, and frontotemporal dementia.

In certain embodiments, the method comprises administering to the subject a therapeutically effective amount of at least one Forskolin analogue, or a salt, isomer, prodrug or solvate thereof. In other embodiments, the method comprises administering to the subject a therapeutically effective amount of at least one Forskolin analogue, or a salt, prodrug or solvate thereof, and a therapeutically effective amount of at least one Noopept analogue, or a salt, prodrug or solvate thereof.

In certain embodiments, the at least one Forskolin analogue is a compound selected from the group consisting of:

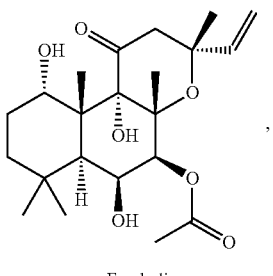

Forskolin

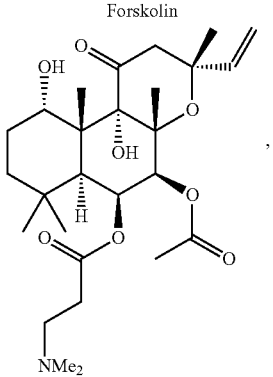

NKH477

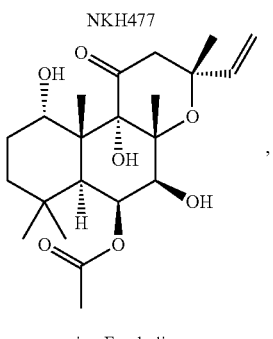

iso-Forskolin

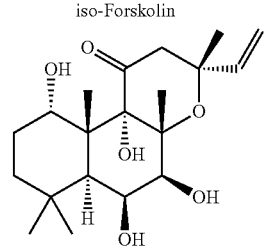

deacetyl-Forskolin, and any deoxygenated derivatives thereof.

In certain embodiments, the therapeutically effective amount of the at least one Forskolin analogue, or a salt, prodrug or solvate thereof, is administered to the subject via an aerosolized formulation. In other embodiments, the therapeutically effective amount of the at least one Forskolin analogue, or a salt, prodrug or solvate thereof, is administered to the subject intranasally. Without intending to be limited to any particular theory, intranasal administration of the at least one Forskolin analogue increases penetration of the blood-brain barrier, and thereby, increases the rate of therapeutic effect in and compliance of the subject. Intranasal delivery can enable rapid and efficient delivery of Forskolin, potentially yielding a therapeutic effect in less than 1 hour, or less than 30 minutes. In yet other embodiments, the at least one Forskolin analogue is administered via other inhalational or pulmonary means. In yet other embodiments, the method comprises administering the at least one Forskolin analogue, or a salt, prodrug or solvate thereof, to the subject orally or intraperitoneally.

In certain embodiments, the at least one Forskolin analogue is administered at least once per day, at least once every two days, at least once every three days, at least once per week or any frequencies and intervals therebetween. In yet other embodiments, the at least one Forskolin analogue is administered intranasally at least once per day to each nostril. In yet other embodiments, the at least one Forskolin analogue is administered from the onset of the neurodegenerative disease or disorder until the subject dies or until symptoms of the neurodegenerative disease or disorder subside.

In certain embodiments, the at least one Noopept analogue is a compound selected from the group consisting of Noopept, piracetam, oxyracetam, aniracetam, and pramiracetam.

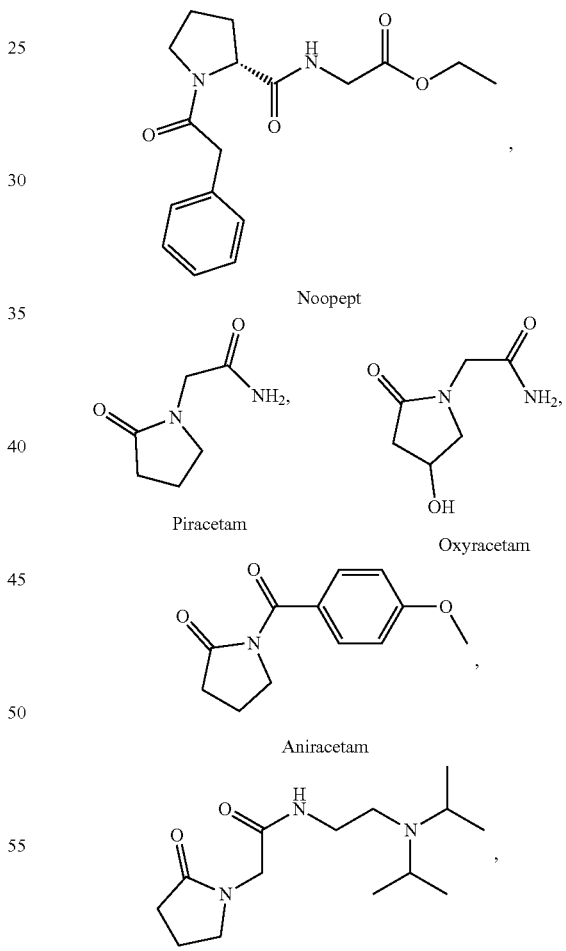

and Pramiracetam.

In certain embodiments, the therapeutically effective amount of the Noopept analogue, or a salt, prodrug or solvate thereof, is administered to the subject orally.

In certain embodiments, the method comprises first administering the therapeutically effective amount of the at least one Forskolin analogue intranasally and then administering the therapeutically effective amount of the at least one Noopept analogue. In other embodiments, the at least one Forskolin analogue is administered intranasally for about 5 days to about 14 days before beginning administration of the therapeutically effective amount of the at least one Noopept analogue.

In certain embodiments, the therapeutically effective amount of the at least one Forskolin analogue, or a salt, prodrug or solvate thereof is about 0.1 mg/kg to about 20 mg/kg. In other embodiments, the therapeutically effective amount of the at least one Forskolin analogue, or a salt, prodrug or solvate thereof, is about 1 mg/kg to about 10 mg/kg. In yet other embodiments, the therapeutically effective amount of the at least one Forskolin analogue, or a salt, prodrug or solvate thereof, is about 0.01 mg to about 100 mg. In yet other embodiments, the therapeutically effective amount of the at least one Forskolin analogue, or a salt, prodrug or solvate thereof, is about 0.1 mg to about 1 mg.

In certain embodiments, the therapeutically effective amount of the at least one Noopept analogue, or a salt, prodrug or solvate thereof, is about 0.05 mg/kg to about 5 mg/kg (Noopept analogue weight/subject body weight). In other embodiments, the therapeutically effective amount of the at least one Noopept analogue, or a salt, prodrug or solvate thereof, is about 5 mg/kg to about 50 mg/kg. In yet other embodiments, the therapeutically effective amount of the at least one Noopept analogue, or a salt, prodrug or solvate thereof, is about 1 mg to about 100 mg. In yet other embodiments, the therapeutically effective amount of the at least one Noopept analogue, or a salt, prodrug or solvate thereof, is about 10 mg to about 30 mg.

In certain embodiments, the therapeutically effective amount of the at least one Forskolin analogue, or a salt, prodrug or solvate thereof, is administered as part of a pharmaceutical composition further comprising at least one pharmaceutically acceptable carrier. In other embodiments, the therapeutically effective amount of the at least one Forskolin analogue, or a salt, prodrug or solvate thereof, is administered as part of an aerosolizable pharmaceutical composition.

In certain embodiments, the pharmaceutical composition comprises at least one Forskolin analogue, or a salt, prodrug or solvate thereof, such that the total Forskolin analogue concentration is about 0.05 mg/ml to about 5 mg/ml. In other embodiments, the pharmaceutical composition comprises at least one Forskolin analogue, or a salt, prodrug or solvate thereof, such that the total Forskolin analogue concentration is about 0.025 mg/ml to about 2.5 mg/ml. In yet other embodiments, the pharmaceutical composition comprises at least one Forskolin analogue, or a salt, prodrug or solvate thereof, such that the total Forskolin analogue concentration is about 0.1 $\mu$M to about 20 $\mu$M. In yet other embodiments, the pharmaceutical composition comprises at least one Forskolin analogue, or a salt, prodrug or solvate thereof, such that the total Forskolin analogue concentration is about 1 $\mu$M to about 10 $\mu$M.

In certain embodiments, the pharmaceutical composition comprises at least one pharmaceutically acceptable solvent selected from, but not necessarily limited to, the group consisting of a buffered aqueous solution, a buffered saline solution, ethanol, water, propylene glycol, polyethylene glycol (PEG), glycofurol, dimethylsulfoxide (DMSO) and (4-(2-hydroxyethyl)-1-piperazineethanesulfonic acid) (HEPES). In yet other embodiments, the pharmaceutical composition further comprises at least one pharmaceutically acceptable salt. In yet other embodiments, the at least one pharmaceutically acceptable salt is selected from, but not necessarily limited to, the group consisting of $K_2HPO_4$, $KH_2PO_4$, NaCl, HCl, sodium benzoate, citrate salts, sulfate salts, and birtartrates salts. In yet other embodiments, the pharmaceutical composition further comprises at least one emulsifying agent. In yet other embodiments, the at least one emulsifying agent is selected from, but not necessarily limited to, the group consisting of polysorbate, polypropylene glycol, polyoxypropylene-polyoxyethylene condensates (Pluronic), glycerol, monostearate, monosodium phosphate and taurocholic acid. In yet other embodiments, the pharmaceutical composition further comprises at least one flavorant or scenting agent such as ethyl laurate, ethyl butyrate, amy acetate, and methyl laureate, and vanilla fragrant agents (vanillin). In yet other embodiments, the pharmaceutical composition further comprises at least one stabilizer or preservative. In yet other embodiments, the at least one preservative is selected from, but not necessarily limited to, benzoic acid, propyl hydroxy benzoic acid, phenol, benzyl alcohol, sodium benzoate, and edentate calcium disodium. In yet other embodiments, the pharmaceutical composition further comprises at least one chelating agent. In certain embodiments, the pharmaceutical composition is a buffered pharmaceutical composition. In other embodiments, the pharmaceutical composition is buffered at a pH of about 7.4.

In certain embodiments, the therapeutically effective amount of the at least one Noopept analogue, or a salt, prodrug or solvate thereof, is administered as part of a pharmaceutical composition further comprising at least one pharmaceutically acceptable carrier. In other embodiments, the therapeutically effective amount of the at least one Noopept analogue, or a salt, prodrug or solvate thereof, is administered as part of pharmaceutical composition for oral administration. In yet other embodiments, the at least one Noopept analogue formulation consists of oral tablets or gel capsules comprising at least one component selected from the group consisting of preservatives, stabilizers, agents, acceptable salts, and emulsifying agents.

In certain embodiments, the method induces recovery of oxidatively-damaged neurons. In other embodiments, the method stimulates dendritogenesis (dendrite outgrowth) and/or neurogenesis (replacement of lost neurons) in part by enhancing the level of the neurogenesis marker doublecortin in the cortex. In yet other embodiments, the method stimulates the recovery of damaged midbrain dopamine and cortical neurons in subjects suffering from Parkinson's disease. Without intending to be limited to any particular mechanism or theory, in certain embodiments, the method enhances PKA-mediated phosphorylation of mitochondrial fission inducer DRP1, thereby promoting phosphorylation of Bcl-2 associated death (BAD) promoter protein and upregulating the PKA-CREB signaling axis. The method shows that intranasal formulation of forskolin enhances neuroprotective PKA activity in the cortex of rats, indicating that intranasal formulation of forskolin crosses the blood brain barrier efficiently.

In certain embodiments, the subject is a mammal. In other embodiments, the subject is a human.

In certain embodiments, the method of the invention is non-toxic to the subject. In other embodiments, the method of the invention is amenable to long term use without causing harm to the subject.

Without intending to be limited by any particular theory, the method of the invention may operate by increasing the level of at least one neurotrophin in the brain of the subject, such as, but not limited to, brain-derived neurotrophic factor (BDNF), nerve growth factor (NGF), and glial cell-derived neurotrophic factor. The dual use of Forskolin and Noopept (or analogues thereof) enhances the level of endogenous BDNF by bypassing the BDNF receptor (TrkB). The increased neurotrophin levels can trigger recovery of damage neurons and growth of new neurons. The method precludes the need to employ exogenous neurotrophic factors to treat disease such as PD. Avoiding the use of exogenous neurotrophic factors is highly desirable because BDNF and GDNF have poor blood-brain barrier traversal properties and low diffusion rates in the cortex and midbrain and therefore have overall low bioavailability in the brain.

The compounds of the invention may possess one or more stereocenters, and each stereocenter may exist independently in either the (R) or (S) configuration. In one embodiment, the compounds described herein are present with the specific stereochemical form illustrated herein. In other embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one embodiment, the compounds of the invention exist as tautomers. All tautomers are included within the scope of the compounds recited herein.

In one embodiment, compounds described herein are prepared as prodrugs. A "prodrug" is an agent converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

Combination and Concurrent Therapies

In one embodiment, the compositions of the invention are useful in the methods of present invention when used concurrently with at least one additional compound useful for preventing and/or treating diseases and/or disorders contemplated herein. In other embodiments, the compounds are administered sequentially or simultaneously in combination.

In one embodiment, the compositions of the invention are useful in the methods of present invention in combination with at least one additional compound useful for preventing and/or treating diseases and/or disorders contemplated herein.

In certain embodiments, the method of the invention further comprises administering to the subject at least one additional agent for the treatment of Parkinson's disease. In other embodiments, the at least one additional agent is selected from the group consisting of cyclic AMP, levodopa (L-dopa), cabidopa, ropinirole, pramipexole, rotigotine, amantadine, trihexyphenidyl, benztropine, selegiline, rasagiline, bromocriptine, tolcapone, pergolide, ropinirole, phenylzine, tranylcypromine, isocarboxazid, entacapone, and artane.

These additional compounds may comprise compounds of the present invention or other compounds, such as commercially available compounds, known to treat, prevent, or reduce the symptoms of diseases and/or disorders contemplated herein. In certain embodiments, the combination of at least one compound of the invention or a salt thereof, and at least one additional compound useful for preventing and/or treating diseases and/or disorders contemplated herein, has additive, complementary or synergistic effects in the prevention and/or treatment of diseases and/or disorders contemplated herein.

As used herein, combination of two or more compounds may refer to a composition wherein the individual compounds are physically mixed or wherein the individual compounds are physically separated. A combination therapy encompasses administering the components separately to produce the desired additive, complementary or synergistic effects.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosing

The regimen of administration may affect what constitutes an effective amount. The therapeutic formulations may be administered to the patient either prior to or after the onset of a disease and/or disorder contemplated herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease and/or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 µg/kg to 100 mg/kg of body weight/per day. One of ordinary skill in the art would be able to study the relevant factors and make the determination regarding the effective amount of the therapeutic compound without undue experimentation.

The compound may be administered to the subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease and/or disorder contemplated herein.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

In some embodiments, the dose of a compound of the invention is from about 0.5 µg to about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of the disease and/or disorder contemplated herein.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease and/or disorder contemplated herein.

Administration

Routes of administration of any of the compositions of the invention include inhalational, oral, and (intra)nasal.

Suitable compositions and dosage forms include, for example, tablets, capsules, caplets, pills, gel caps, troches, emulsions, dispersions, suspensions, solutions, syrups, granules, beads, gels, powders, pellets, magmas, lozenges, liquid sprays for nasal or oral administration, dry powder or aerosolized formulations for inhalation, and the like. It should be understood that the formulations and compositions that would be useful in the present invention are not limited to the particular formulations and compositions that are described herein.

Pulmonary Administration/Intranasal Administration

A pharmaceutical composition of the invention may be prepared, packaged, or sold in a formulation suitable for pulmonary administration via the buccal cavity. Such a formulation may comprise dry particles that comprise the active ingredient and have a diameter in the range from about 0.5 to about 7 nanometers, and in certain embodiments from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In certain embodiments, such powders comprise particles wherein at least 98% of the particles by weight have a diameter greater than 0.5 nanometers and at least 95% of the particles by number have a diameter less than 7 nanometers. In certain embodiments, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in certain embodiments having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring, a volatile oil, a buffering agent, a surface-active agent, or a preservative. The droplets provided by this route of administration in certain embodiments have an average diameter in the range from about 0.1 to about 200 nanometers.

The pharmaceutical composition of the invention may be delivered using an inhalator such as those recited in U.S. Pat. No. 8,333,192 B2, which is incorporated herein by reference in its entirety.

The formulations described herein as being useful for pulmonary delivery may also be useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

Pharmaceutical compositions of the invention formulated for intranasal delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring, a volatile oil, a buffering agent, a surface-active agent, or a preservative. The droplets provided by this route of administration in certain embodiments have an average diameter in the range from about 0.1 to about 200 nanometers.

In one embodiment, a liquid formulation is delivered by using an intranasal atomizer, optionally with a malleable stylet and soft conical plug to prevent the expulsion of excess liquid from the nose. A vial containing lyophilized form of the active ingredient can be diluted in sterile phosphate buffered saline buffer (pH 7.4), or a similar polar buffer, using a sterile gaged syringe and inserted into the nasal spray plug prior to administering to the patient intranasally.

Oral Administration

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent. In certain embodiments, Noopept and any analogues thereof, can be administered orally according to any of the above recited embodiments.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Kits

In another aspect, the invention further provides a kit comprising at least one pharmaceutical composition of the invention, an applicator, and instructional material for use thereof. The instructional material included in the kit comprises instructions for carrying out the method of the invention to prevent or treat a neurodegenerative disorder or disease in a subject.

In certain embodiments, the kit comprises at least one dose of a pharmaceutical composition comprising at least one Forskolin analogue or a salt, prodrug or solvate thereof, as described elsewhere herein. In other embodiments, the kit comprises at least two doses of the pharmaceutical composition comprising at least one Forskolin analogue or a salt, prodrug or solvate thereof, each in a pre-packaged single dose formulation. In yet other embodiments, the kit comprises the at least one dose of a pharmaceutical composition comprising at least one Forskolin analogue or a salt, prodrug or solvate thereof in lyophilized form. In yet other embodiments, the kit further comprises a pharmaceutically acceptable carrier or solvent for reconstituting the lyophilized pharmaceutical composition.

In certain embodiments, the kit further comprises at least one dose of a pharmaceutical composition comprising the at least one Noopept analogue, or a salt, prodrug or solvate thereof, as described elsewhere herein. In other embodiments, the at least one dose of a pharmaceutical composition comprising the at least one Noopept analogue, or a salt, prodrug or solvate thereof, is formulated as part of an oral tablet or gel capsule, as described elsewhere herein.

In certain embodiments, the kit provides at least one dose each of a pharmaceutical composition comprising at least one Forskolin analogue, or a salt, prodrug or solvate thereof, and a pharmaceutical composition comprising at least one Noopept analogue, or a salt, prodrug or solvate thereof. In other embodiments, the kit further provides instructional material for administering the pharmaceutical compositions to a subject such that the compositions are administered in sequence or in conjunction.

In certain embodiments, the applicator is a nebulizer, inhalator, atomizer or analogous device adapted for intranasal delivery of the pharmaceutical composition comprising the at least one Forskolin analogue, or a salt, prodrug or solvate thereof.

In certain embodiments, the kit further comprises at least one additional agent useful to treat a disease or disorder contemplated within the invention.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Instructional material" as used herein includes a publication, a recording, a diagram, or any other medium of expression that can be used to communicate the usefulness of a composition and/or compound of the invention in a kit. The instructional material may describe a method of using the composition and/or compound of the invention in a method of the invention. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The terms "patient," "subject" or "individual" are used interchangeably herein, and refer to any animal, or cells thereof whether in vitro or in situ, amenable to the methods described herein. In a non-limiting embodiment, the patient, subject or individual is a human. In other embodiments, the patient is a non-human mammal including, for example, livestock and pets, such as ovine, bovine, porcine, canine, feline and murine mammals. In yet other embodiments, the patient is an avian animal or bird. Preferably, the patient, individual or subject is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "therapeutically effective amount" refers to an amount that is sufficient or effective to prevent or treat (delay or prevent the onset of, prevent the progression of, inhibit, decrease or reverse) a disease or condition described or contemplated herein, including alleviating symptoms of such disease or condition.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range.

The following abbreviations are used herein:
BDNF brain-derived neurotrophic factor
dbt-cAMP dibutyryl cyclic AMP
DMSO dimethyl sulfoxide
ECARS extracellular acidification rates
LBD Lewy Body Dementia
L-DOPA Levodopa
NGF nerve growth factor
PD Parkinson's Disease
OCRs oxygen consumption rates
TH tyrosine hydroxylase Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

It is to be understood that, wherever values and ranges are provided herein, the description in range format is merely for convenience and brevity and should not be construed as an inflexible limitation on the scope of the invention.

Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Materials and Methods
Materials

Rotenone, Noopept and Forskolin were purchased from SIGMA-Aldrich and used without further purification. Mitochondrial Stress Kits, including antimycin A, Carbonyl cyanide-4-phenylhydrazone (FCCP), rotenone and oligomycin, were purchased from Agilent Technologies.

Neuron Culturing Procedures

Primary cortical and midbrain neurons were prepared from wild-type C57BL/6 or Pink1 knockout mice as previously described (Dagda et al, Cell Death Differ, 2011 December; 18(12): 1914-1923), using procedures to minimize distress that have been approved by the University of Nevada, Reno Institutional Animal Care and Use Committee (IACUC). Primary cortical and midbrain neurons were prepared from 14-day C57BL/6 mouse embryos (Hilltop Laboratory Animals, Scottdale, Pa., USA) and control littermates. Approximately, 16 wells of 85,000-100,00 cells/well were obtained from six to eight embryos (male and female) per timed pregnant female for midbrain cultures or roughly 10× as many total cortical cells from eight embryos plated at 100,000 cells per well for most experiments described on this patent application. After 3 days, two-thirds of the media was exchanged with fresh Neurobasal (Gibco/Invitrogen, Carlsbad, Calif., USA) containing B27 and 0.75 mM L-glutamine.

Rotenone Formulation/Rotenone Administration

Rotenone (1.26 mM stock, Sigma, Cat #R8875) was freshly prepared in water prior to each use. Stocks of rotenone were maintained in the dark at −20° C. for up to 6 months. Rotenone was used at 65 µM for neuroblastoma cells and at 65 nM for primary cortical neurons for 4-6 hours to induce oxidative and autophagic stress.

Animal Handling Procedures

All experiments involving mice and rats were performed in accord with ARRIVE (Animal Research: Reporting of In Vivo Experiments) guidelines. Wild-type C57BL/6 and PINK1 knockout mice (B6.129S4-Pink1$^{tm1Slm}$/J), wild-type (Long Evans rats) and PINK1 knockout (LEH-PINK1$^{tm1sage}$.Park6) rats (SAGE labs through Horizon Discovery) were handled humanely and appropriately per the ARRIVE guidelines. All mice were housed at the Laboratory of Animal Resources (University of Nevada, Reno) in cages containing sufficient bedding, food (pellets), water, with sufficient social, nutritional and "enriched" environments, and maintained in HVAC-pressurized/sterile environment and in 12:12 hr light/dark cycles.

To culture primary cortical neurons from mouse embryos, pathogen specific free (SPF) timed pregnant mice (E14) were purchased and supplied from Charles Rivers Laboratories (Reno, Nev.).

Forskolin Formulation

Forskolin (Coleus forskohlii, >98% HPLC, Sigma Aldrich) was prepared in DMSO as 5 mg/ml stocks (stable for up to 6 months if kept in the dark and stored in −20° C. until ready to use). On the day of the experiment, the forskolin aliquot was thawed and cells were treated once with forskolin at a concentration of 1 to up to 10 µM of forskolin in complete media for treating primary cortical neurons or for intraperitoneal administration of PINK1 knockout mice or PINK1 knockout rats.

For intranasal delivery of forskolin, intranasal formulation of forskolin was prepared as described in Example 6.

Noopept Formulation

Noopept (>98% HPLC, Sigma Aldrich) was prepared in DMSO as 20 mg/ml stock solutions (stable for up to 6 months if kept in the dark and stored at −20° C. until ready to use). On the day of the experiment, the Noopept aliquots were thawed and cells were treated once with Noopept at the indicated concentrations (20 nM) in complete media for treating primary cortical Neurons or for intraperitoneal administration of PINK1 knockout mice or PINK1 knockout rats.

Measuring PKA Activity from Brain Lysates

PKA activity was measured in cortex of wild-type Long Evans Hooded rats by determining the level of PKA-mediated substrate phosphorylation by using an ELISA-based colorimetric PKA activity kit per manufacturer's recommendations (Enzo Life Sciences; ADI-EKS-390A) with the following minor modifications. To determine PKA-specific activity, lysates form the cortex were treated with H89, a pharmacological inhibitor of PKA at 10 µM for 5 min, and the H89-resistant kinase activity was subtracted from total kinase activity of untreated tissue lysates.

Statistical Analysis

Unless indicated otherwise, results are expressed as mean±S.E.M. (standard errors of mean) from three independent experiments. Data was analyzed by Student's t test (two-tailed) for pairwise comparisons. Multiple group comparisons were done by performing one-way ANOVA followed by Bonferroni-corrected Tukey's test. P values less than 0.05 were considered statistically significant.

Power Analyses

For immunohistochemistry analyses using western blot, a total sample size of 8 (4 mice per group) was required based on preliminary data which yielded a large effect size (Cohen's d=1.99, β: 0.80 and α=0.05).

Example 1: Forskolin Treatment of PD Model Neurons

Figure 2:
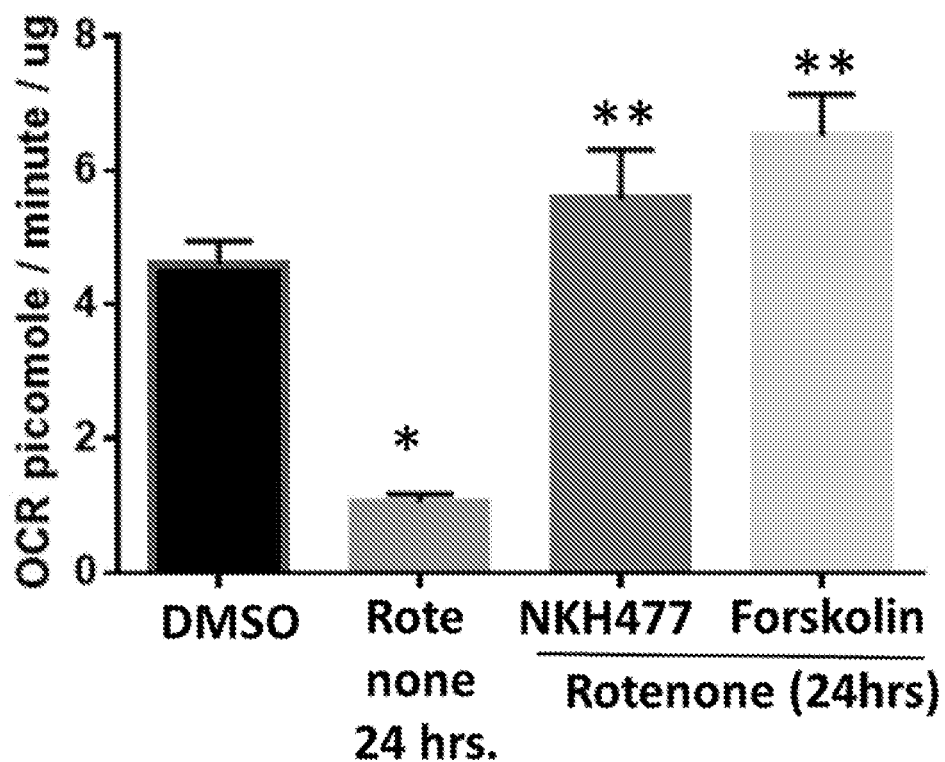
FIG. 2 is a graph showing that Forskolin significantly restored spare respiratory capacity in primary cortical neurons treated with rotenone.

Primary cortical neurons seeded at a cell density of 85,000 to 100,000 cells per well were exposed with an LD50 concentration of rotenone (65 nM), a chemical model of Parkinson's disease, for 24 hours. Rotenone-treated primary neurons were then exposed to 250 μM dibutyryl cyclic AMP (dbt-cAMP) or with the parental or water-soluble form (NKH477) of Forskolin (6.5 μM-8.5 μM, 24 hrs). The basal oxygen consumption rates (OCRs), a proxy for mitochondrial function, were analyzed by using an XF24$^e$ Extracellular Flux Analyzer (Agilent Technologies). The maximal oxygen consumption rates (OCRs), a proxy for maximal buffering capacity of mitochondrial function, were also analyzed by using an XF24$^e$ Extracellular Flux Analyzer in primary cortical neurons treated with 1 μM FCCP, an ionophore that acts as a mitochondrial uncoupler. While rotenone induced a significant reduction in baseline OCR reduction and spare respiratory capacity (Maximal OCRs-Baseline OCRs), treating primary cortical neurons with Forskolin or with the water-soluble forskolin analogue NKH477 partially or completely restored baseline mitochondrial respiration (FIG. 1) and completely restored spare respiratory capacity (FIG. 2) (*:$p<0.05$ vs. DMSO control, **:$p<0.05$ vs. rotenone, One-Way ANOVA, data pooled from 20 wells/group collected from three independent experiments).

Figure 3:
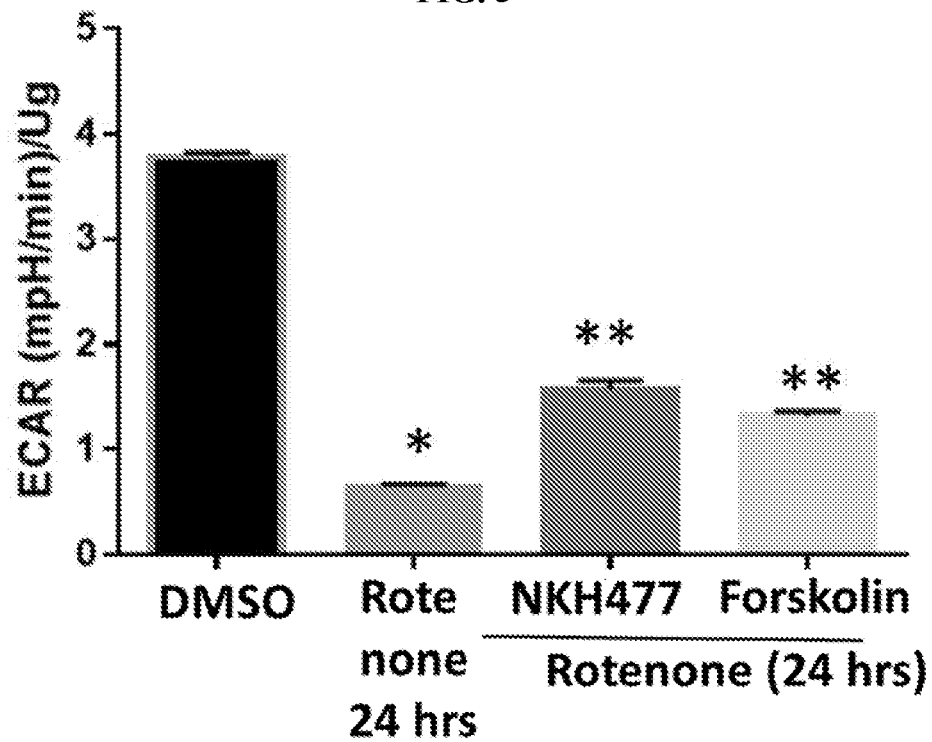
FIG. 3 is a graph showing that Forskolin significantly restored glycolysis in primary cortical neurons treated with rotenone.

The extracellular acidification rates (ECARs), a proxy for glycolysis, were also assessed by using an XF24$^e$ Extracellular Flux Analyzer in primary neurons. While rotenone induced a significant reduction in baseline ECARs, treating primary cortical neurons with Forskolin or with the water-soluble forskolin analogue NKH477 completely restored normal glycolytic function (FIG. 3) (*:$p<0.05$ vs. DMSO control, **:$p<0.05$ vs. rotenone, One-Way ANOVA, data pooled from 20 wells/group collected from three independent experiments).

Figure 4:
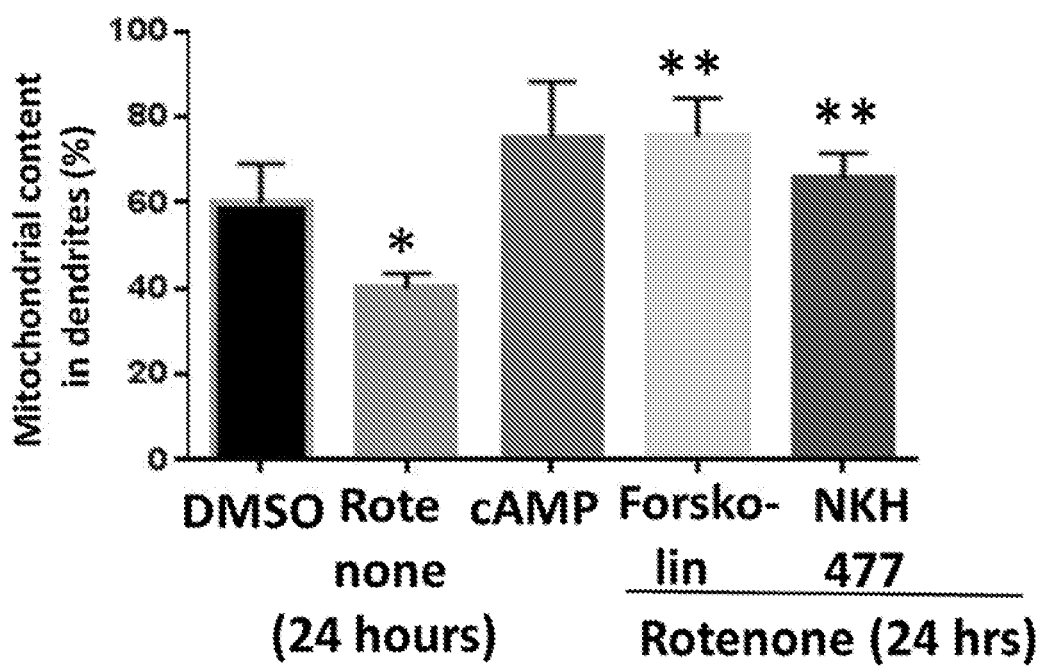
FIG. 4 is a graph showing that Forskolin significantly restored mitochondrial content in dendrites of primary cortical neurons treated with rotenone.

The rotenone-treated neurons were also studied by image-based analyses of mitochondrial content in dendrites from primary cortical neurons immunostained for dendrites (MAP2B) and for mitochondria (TOM20). The images showed that treatment of neurons with Forskolin or dbt-cAMP reversed the loss of mitochondria within dendrites (FIG. 4). Additionally, dendrite length analysis in fixed primary cortical neurons, immunostained for dendrites (MAP2B), showed that Forskolin or dbt-cAMP treatment reversed the loss of dendrites (FIG. 5) (*:$p<0.05$ vs. DMSO control, **:$p<0.05$ vs. rotenone, One-Way ANOVA, 12 wells compiled from three independent experiments). Overall, the data showed that eliciting PKA signaling is sufficient to reduce the loss of mitochondria in dendrites and restore dendrite arbors in primary cortical neurons.

The metabolic data (FIGS. 1-3) support the ability of Forskolin to act as a nootropic agent by stimulating glycolysis and mitochondrial respiration in primary neurons. Concentrations of Forskolin greater than 12.5 μM did not confer significant protection against rotenone-mediated neurodegeneration. This observation suggests that Forksolin protects against the loss of neuronal metabolism (oxidative phosphorylation and glycolysis) in a bimodal manner with maximal effects observed at a concentration of about 10 μM.

Figure 5:
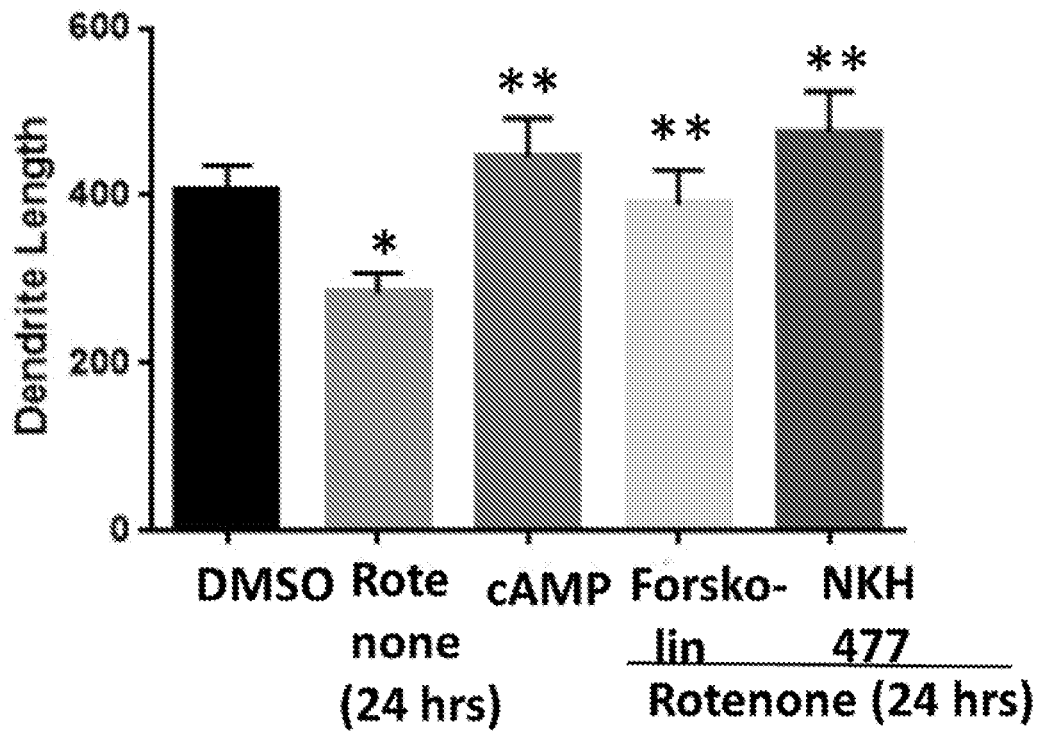
FIG. 5 is a graph showing that Forskolin significantly restored dendrite connectivity in primary cortical neurons treated with rotenone.

Treating primary cortical neurons with either the parental or water soluble form (NKH477) of Forskolin completely blocked rotenone-mediated loss of dendrite arbors (total dendrite length per neuron) and mitochondrial levels in dendrites (% of dendrites occupied by mitochondria) induced by rotenone-mediated toxicity compared to untreated primary neurons (FIGS. 4-5).

Example 2: Forskolin Treatment of PD Model Mice

Figures 6A, 6B:
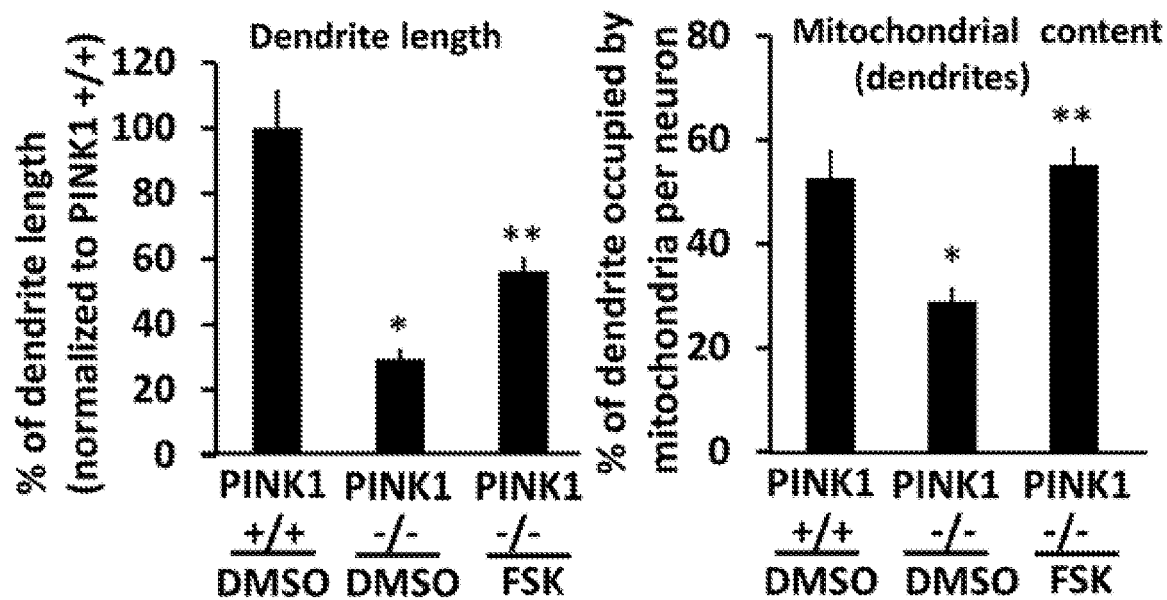
FIGS. 6A-6B are graphs showing that PINK1 knockout mice treated with Forskolin reverses the loss of dendrites and mitochondria in dendrites of midbrain dopamine neurons.

Wild-type (PINK1+/+) or PINK1 knockout (PINK1−/−) mice were treated with intraperitoneal injections of DMSO control or Forskolin (1 mg/kg body weight) once every 2 days for up to one week. At the end of each treatment, mice were sacrificed, and intracardially perfused with saline followed by 4% formaldehyde. Midbrain slices from wild-type and PINK1 KO mice were immunostained for mitochondria (TOM20) and tyrosine hydroxylase (TH, purple) to identify midbrain dopamine neurons and dendrite length. Image-based quantitation of immunostained dendrites and mitochondria in substantia nigra dopamine neurons show that administration of Forskolin significantly increased dendrite length (FIG. 6A) and mitochondrial content (FIG. 6B) in dendrites compared to untreated PINK1 knockout mice and to similar levels as wild-type mice (*:$p<0.05$ vs. PINK1+/+ mice, **: $<0.05$ vs. PINK1−/− mice, ONE-Way ANOVA, 3-4 mice per group).

Example 3: Combined Forskolin and Noopept Treatment of PD Model Neurons

Figure 7:
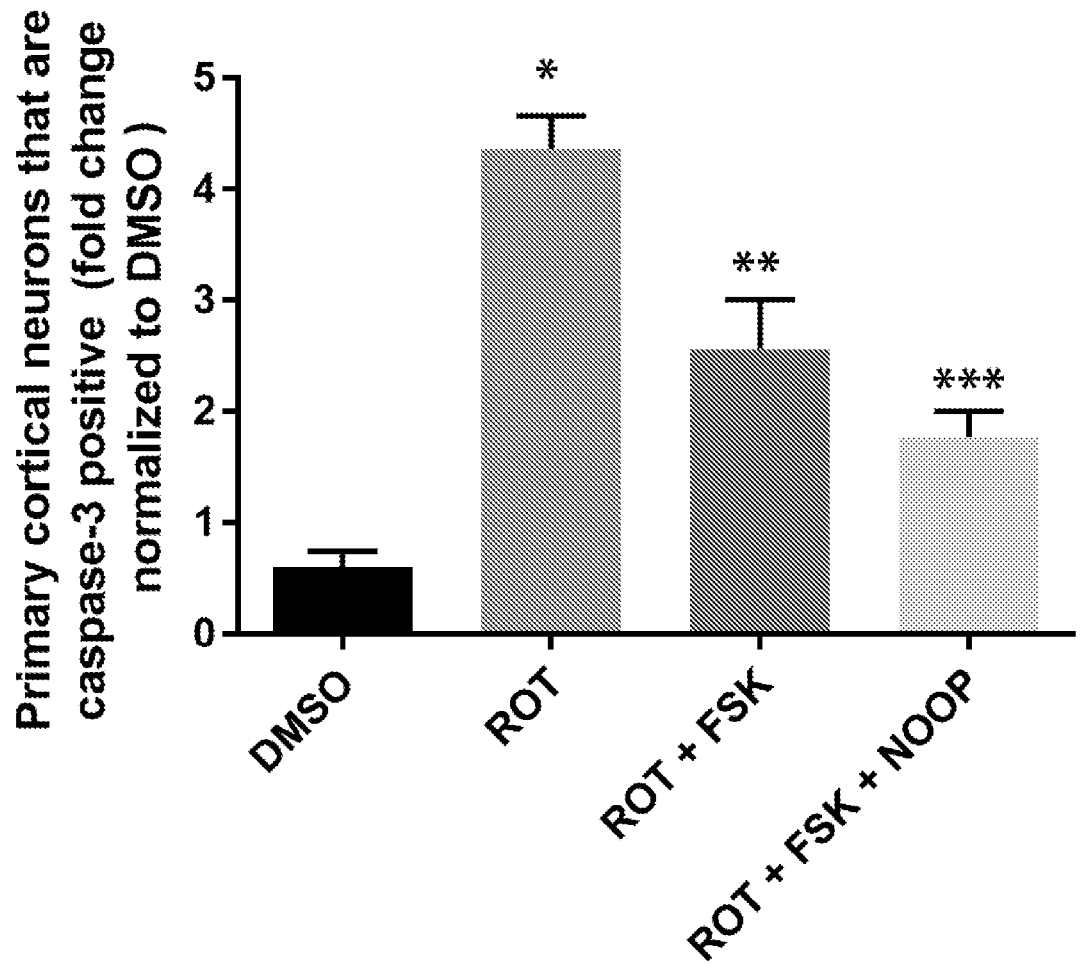
FIGS. 7-8 are graphs showing that sequentially treating primary cortical neurons (FIG. 7) and midbrain neurons (FIG. 8) with Forskolin and Noopept has an increased neuroprotective effect compared to Forskolin treatment alone.

A first batch of primary cortical neurons seeded at a cell density of 85,000 to 100,000 cells per well were exposed with an LD50 concentration of rotenone (65 nM) for 24 hours. Rotenone pre-treated primary neurons were then exposed to Forskolin (6.5 μM-8.5 μM, 24 hrs) or treated with Forskolin (10 μM) for 24 hrs followed by Noopept (23.5 nM) for another 5.5 hrs. Following treatments, primary cortical neurons were fixed in paraformaldehyde and immunostained for active caspase-3 and cells were identified with DAPI counterstain (less than 10% of the cells were found to be glia). The percentage of DAPI positive primary cortical neurons that were caspase-3 positive were quantified and normalized to untreated neurons (FIG. 7) (*:$p<0.05$ vs. DMSO control, :$p<0.05$ vs. rotenone, *:$p<0.05$ vs. rotenone and Forskolin, One-Way ANOVA, 25 epifluorescence fields per group compiled from one independent experiment).

Figure 8:
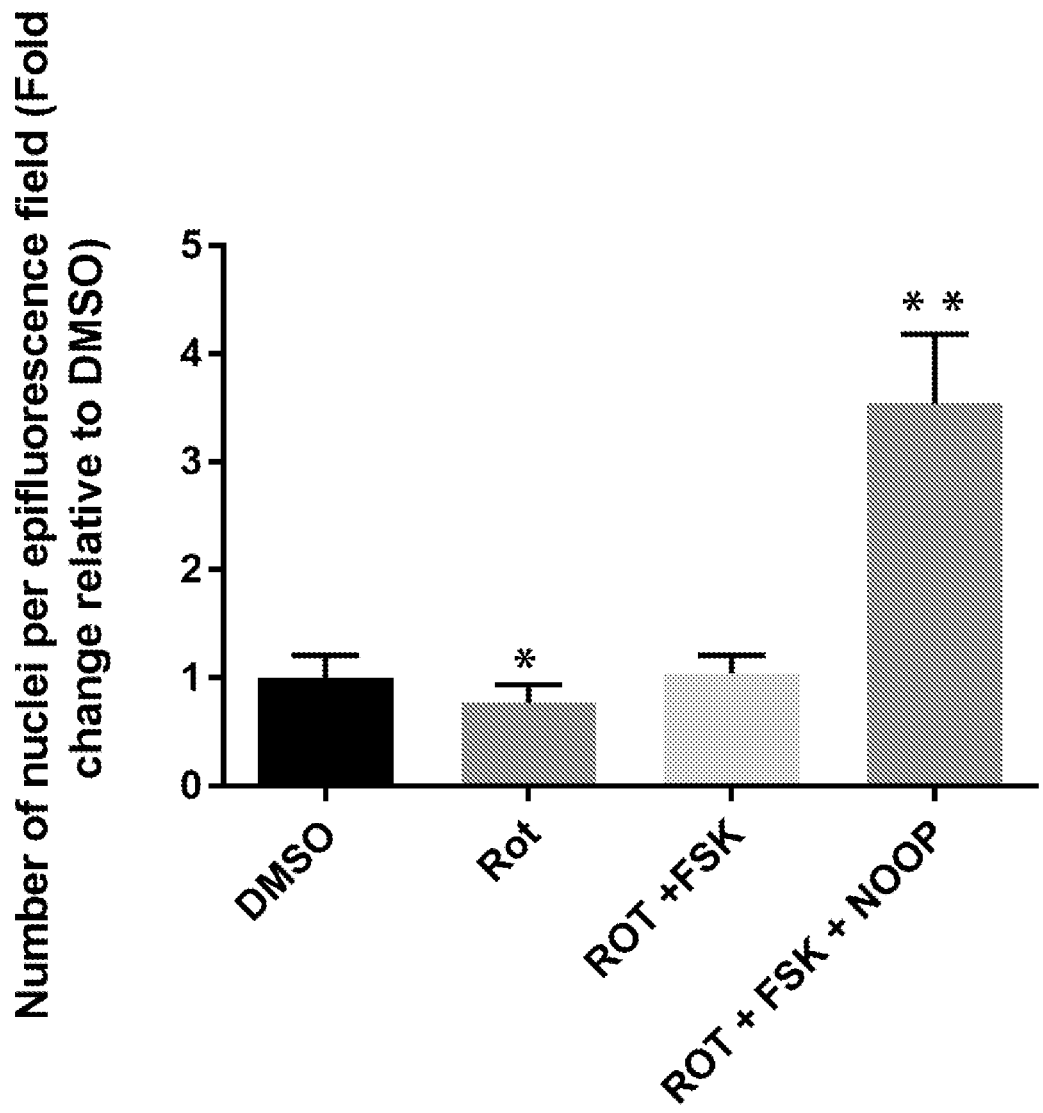

A second batch of primary cortical neurons seeded at a cell density of 85,000 to 100,000 cells per well were exposed with an LD50 concentration of rotenone (65 nM) for 24 hours. Rotenone-treated primary neurons were then exposed to Forskolin (6.5 μM-8.5 μM, 24 hrs) followed by Noopept (10 nM) for another 10 hours. Following treatments, dopaminergic midbrain neurons were fixed in paraformaldehyde, immunostained for the neuronal marker Tyrosine Hydroxylase (TH) to identify midbrain dopaminergic neurons and counterstained with DAPI to identify neurons. FIG. 8 shows the average number of nuclei (DAPI) per epifluorescence field per experimental condition (*:$p<0.05$ vs. DMSO control, :$p<0.05$ vs. rotenone, *:$p<0.05$ vs. rotenone and Forskolin, One-Way ANOVA, 25 epifluorescence fields compiled from one independent experiment).

Figure 9:
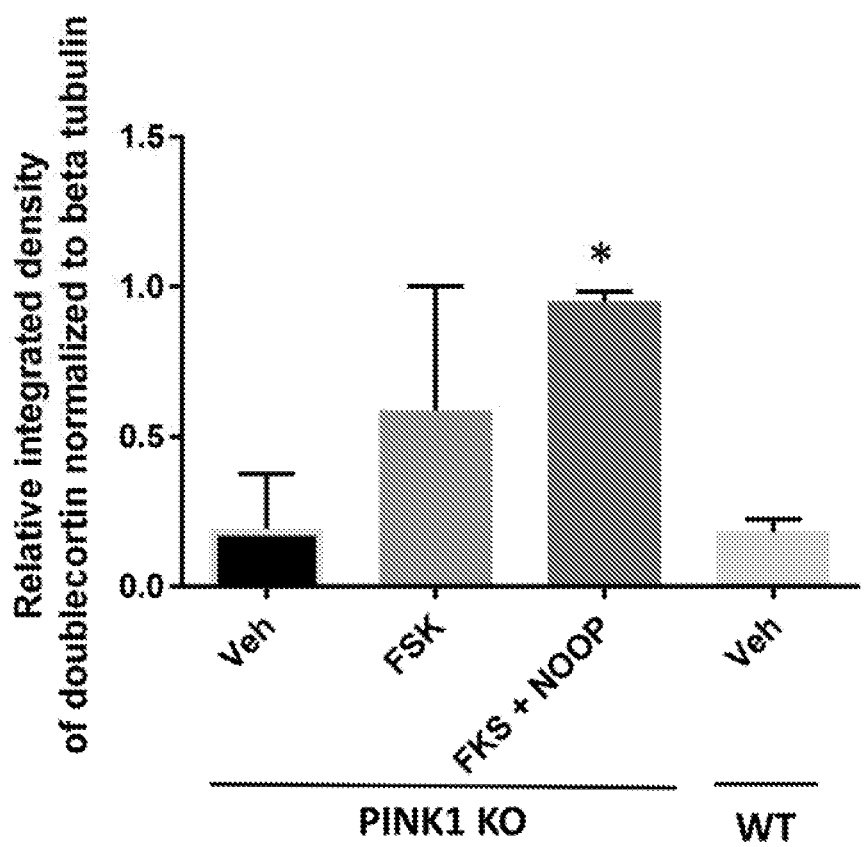
FIG. 9 shows that treating PINK1 knockout mice with Forskolin and Noopept significantly increases neurogenesis as noted by an increase in the protein level of the neurogenesis marker doublecortin in the cortex of PINK1-KO mice compared to untreated or Forskolin-treated PINK1-KO mice.

Example 4: Combined Treatment Stimulates Neurogenesis in the Cortex of PINK1-KO Mice Wild-type (PINK1+/+) or PINK1 knockout (PINK1−/−) mice were treated with intraperitoneal injections of DMSO control or Forskolin (1.6 mg/kg body weight) once every 2 days for up to 10 days or with Forskolin (1.6 mg/kg body weight) for two doses (once every two days) followed by combined treatment with Forskolin and Noopept (0.05 μg/kg) for three more doses (once every two days). At the end of each treatment, mice were sacrificed, and intracardially perfused with saline. The cortices were harvested, lysed, homogenized and up to 25 μg of protein per animal were electrophoresed on 10% acrylamide gels and immunoblotted for doublecortin, a neurogenesis marker predominantly expressed in immature/migrating cortical neurons. FIG. 9 shows a bar graph of the mean integrated density of the immunoreactive bands specific for doublecortin. (*:p<0.05 vs. PINK1-KO/Veh, N=3-4 animals per group, One-Way ANOVA, Tukey's test).

The data shows that treating PINK1-KO mice with Forskolin and Noopept, but not Forskolin alone, can significantly enhance the protein levels of doublecortin, suggesting that Noopept stimulates neurogenesis in the cortex of PINK1-KO mice.

Example 5: Combined Treatment of PINK1 Knockout Rats with Forskolin and Noopept Reverses Motor Symptoms of Neurodegeneration and Neurodegeneration Wild-type (PINK1+/+) or PINK1 knockout (PINK1−/−) rats were treated with intraperitoneal injections of DMSO control or of Forskolin (1.6 mg/kg body weight) once every 2 days for two doses followed by co-administration with Noopept (0.05 μg/kg) for three more doses (once every two days) for up to a total treatment time of 10 days. At the end of each treatment, a battery of motor tests were performed in vehicle-treated or WT and PINK1-KO rats treated with compounds to analyze for muscle strength in hind legs by using a grip strength analyzer. In addition, muscle coordination and balance were assessed by subjecting the rats to cross a 1-meter, tapered beam balance (2 cm width) for up to three trials per animal.

Figure 10:
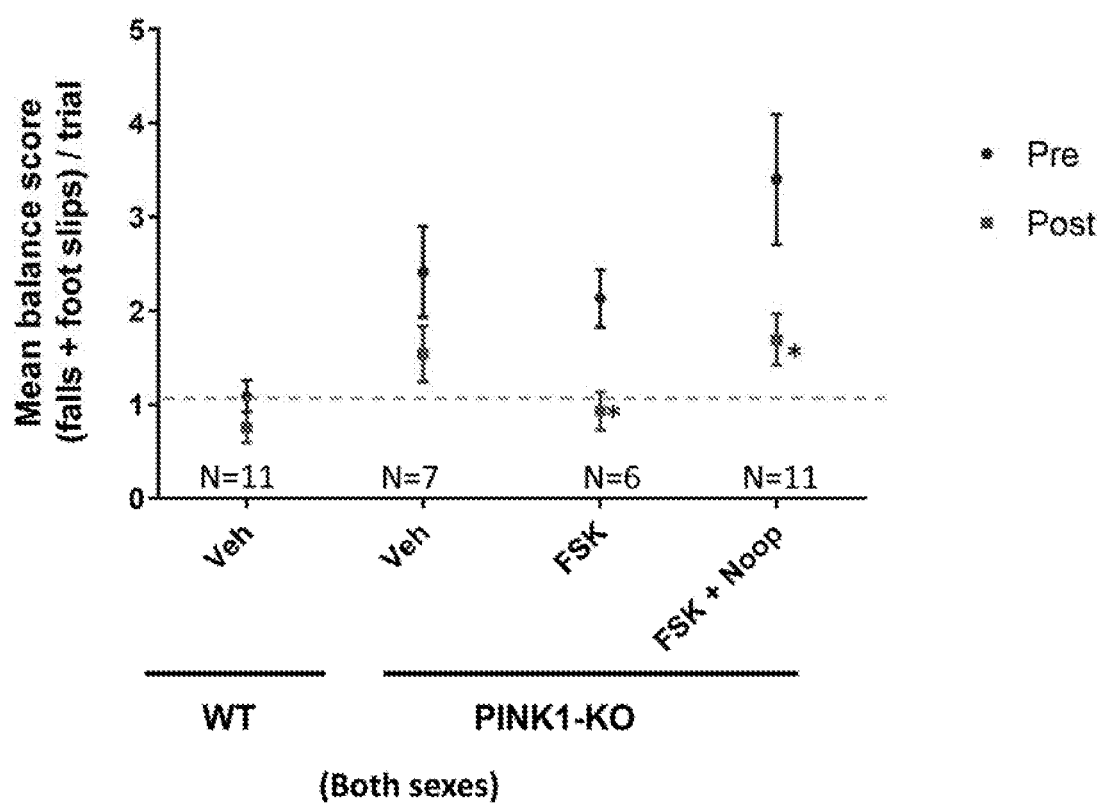
FIG. 10 shows that intraperitoneal administration of Forskolin, or of Forskolin and Noopept, can reverse the loss of balance and coordination in PINK1-KO rats, an in vivo model of Parkinson's disease that shows robust motor symptoms of PD and neurodegeneration.

FIG. 10 shows the mean motor score (falls and slips per crossing) per group of rats before and after treatment with compounds (Forskolin and/or Noopept). The motor score employed to quantify coordination and balance in rats entailed the following: a score of 1.0 was assigned to rats that showed one slip per crossing whereas a score of 2.0 was assigned to each rat that fell off the beam balance during a trial. Both motor parameters were added for each rat for three trials and averaged per treatment group of animals (*:p<0.05 vs. pre-treatment (pre), paired t-test, N=6-11 rats per group). The data suggest that treating Parkinsonian rats (PINK1-KO) with intraperitoneal injections of Forskolin or of both compounds (Forskolin and Noopept) for 10 days can reverse the loss of coordination and balance (falls and slips per crossing of the beam).

Figure 11:
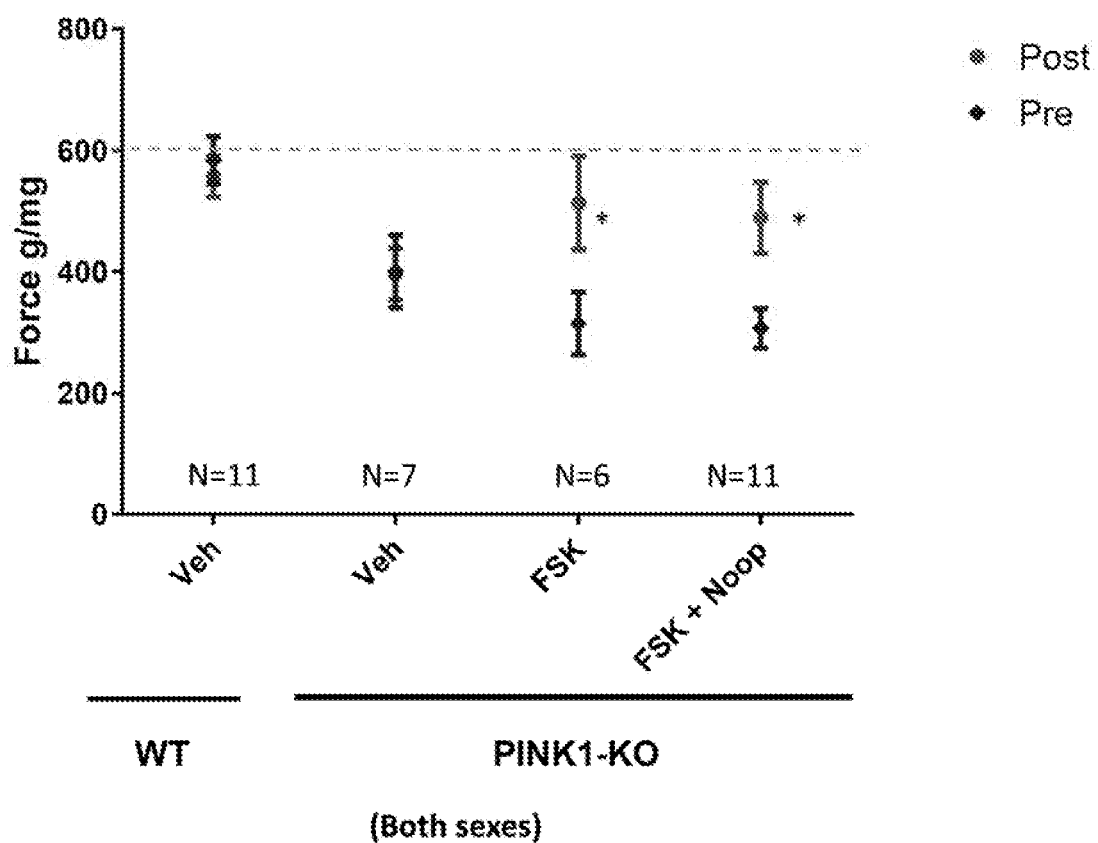
FIG. 11 shows that intraperitoneal administration of Forskolin, or of Forskolin and Noopept, can reverse the loss of muscle strength in the hind limbs of PINK1-KO rats.

FIG. 11 shows the mean strength (force g/kg of weight) of hind legs per group of rats derived from the compiled average of three trials per animal. (*:p<0.05 vs. pre-treatment (pre), paired t-test, N=6-11 rats per group). The data suggest that treating Parkinsonian rats (PINK1-KO) with intraperitoneal injections of Forskolin or of both compounds (Forskolin and Noopept) for 10 days can reverse the loss of hind limb strength whereas injecting vehicle control (PBS) does not have an effect in Parkinsonian rats.

Figure 12:
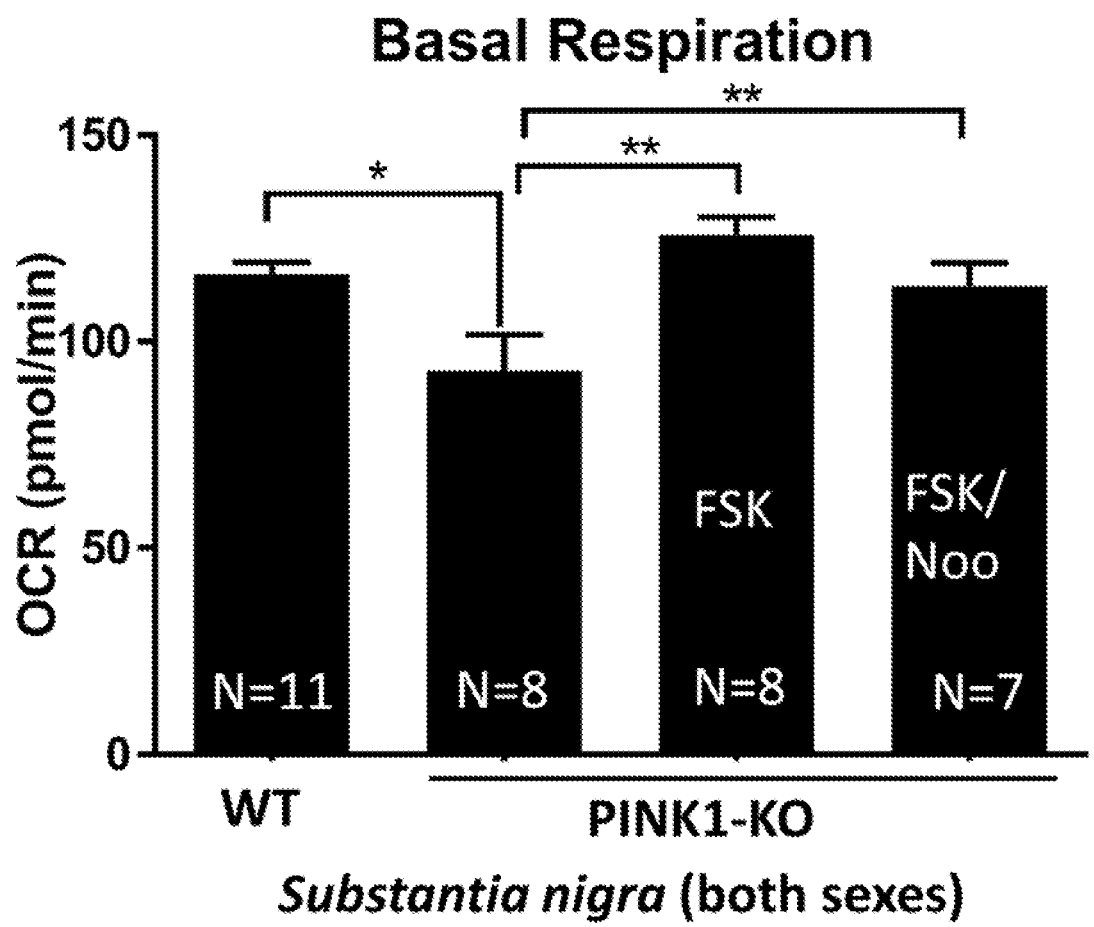
FIG. 12 shows that intraperitoneal administration of Forskolin, or of Forskolin and Noopept, significantly restored basal respiration in the midbrain of PINK1-KO rats.

Upon completing the behavioral tests, the rats were then transcardially perfused with phosphate buffered saline, and the brains were extracted, midbrain slices were generated by using a vibratome (brain slicer) at room temperature and maintained in artificial cerebral spinal fluid. The oxygen consumption rates were then measured by using an XF24$^e$ Metabolic Analyzer to measure energy production in the brain (oxidative phosphorylation) as described in Example 1 but with the following modifications. To measure the bioenergetics profile of midbrain slices derived from Parkinsonian or wild-type rats, biopsy punches of 1.2 mm diameters from each brain regions were carefully isolated and mounted on the bottom of each well from the plate. Mesh capture screens, previously submerged in XF Base Medium were carefully mounted immediately over the tissue and 700 μL of Agilent Seahorse XF Base Medium (supplemented with 2 mM L-glutamine, 1 mM Na pyruvate, 10 mM glucose and 4 mg/ml BSA, pH 7.4) was added into each well. The brain slices were analyzed for baseline respiration for five cycles with each cycle consisting of 3 min. of mixing, 3 min. of waiting and 2 min. of measuring OCRs. FIG. 12 shows a graph of the mean baseline oxygen consumption rats (OCRs) in midbrain slices from Parkinsonian rats treated intraperitoneally with vehicle control (PBS), with Forskolin (1.6 mg/kg) or with Forskolin (1.6 mg/kg) and Noopept (0.05 μg/kg).

(*:p<0.05 vs. WT, **: p<0.05 vs. PINK1-KO/untreated, One-Way ANOVA, Tukey's test, N=7-11 rats from both sexes per group). The data shows that intraperitoneal injections with Forskolin or with Forskolin and Noopept is sufficient to reverse the loss in oxidative phosphorylation in the midbrain of Parkinsonian rats.

Figure 13:
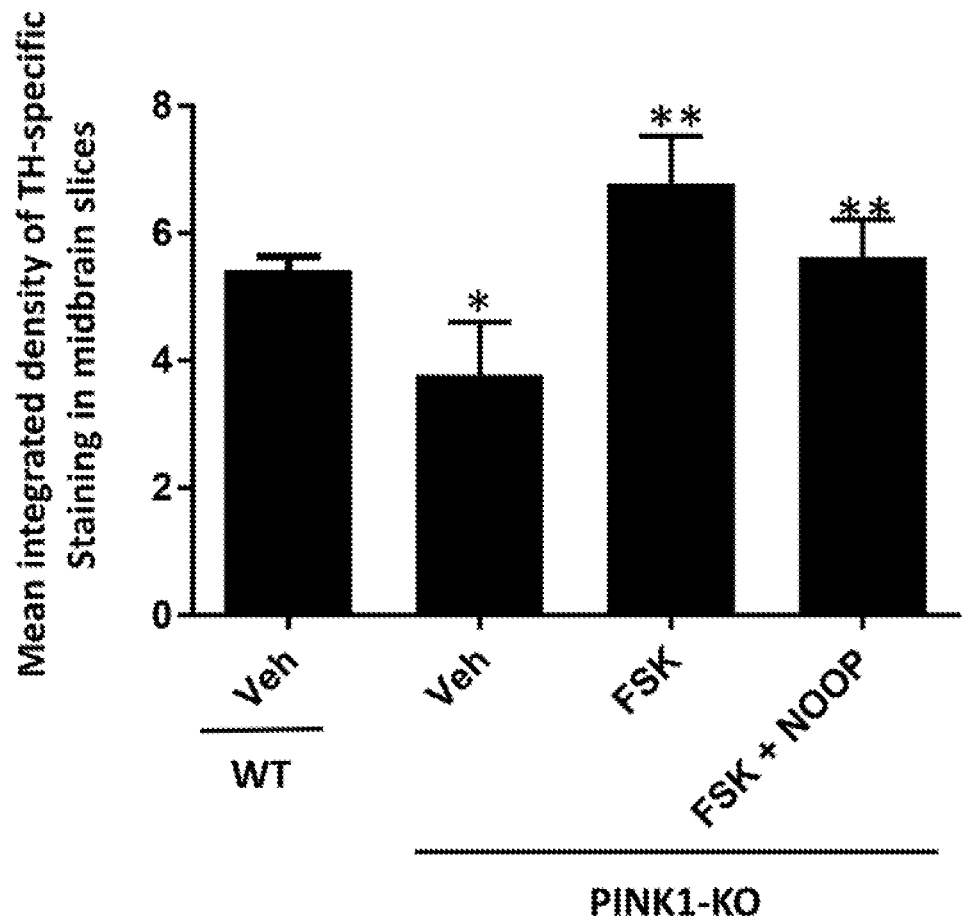
FIG. 13 shows intraperitoneal administration of Forskolin, or of Forskolin and Noopept, significantly reversed neurodegeneration of substantia nigra dopamine neurons in the midbrain of PINK1-KO rats.

Another group of wild-type and PINK1-KO rats were sacrificed, and intracardially perfused with saline followed by 4% formaldehyde. Midbrain slices from wild-type and PINK1-KO rats were immunostained for tyrosine hydroxylase (TH, purple) to identify midbrain dopamine neurons. Image-based quantitation of the abundance of TH-positive neurons was assessed by measuring the integrated density of TH staining for each midbrain slice by image analysis by using NIH Image J. FIG. 13 shows a bar graph of the compiled mean integrated density of TH-specific immunofluorescence in midbrain slices from vehicle treated, Forskolin (1.6 mg/kg) or Forskolin (1.6 mg/kg) and Noopept (0.05 μg/kg), treated female PINK1-KO rats. (*:p<0.05 vs. WT/vehicle, **:p<0.05 vs. PINK1-KO/vehicle, One-Way ANOVA, Tukey's test, N=4-7 rats per group). The data shows that intraperitoneal administration of Forskolin or of Forskolin and Noopept completely reverses the loss of midbrain dopamine neurons in Parkinsonian rats. These data shows that Forskolin and Noopept reverses neurodegeneration in an in vivo model of PD.

Example 6: Aerosolized Forskolin Formulations

The invention provides aerosolizable formulations suitable for intranasal delivery of Forskolin to a subject as listed below.

Water Soluble Forskolin in Phosphate Buffered Saline

Combine 1.68 grams $K_2HPO_4$ (60 nM), 5.28 grams $KH_2PO_4$ (40 nM), and 81.8 grams NaCl (1.4 nM). Add distilled $H_2O$ up to 1 L total volume. Autoclave and sterilize solution. Adjust the pH of the solution to 7.4 using a pH meter. Add 1 gram sodium benzoate (0.1%) or propyl benzoic acid. Reconstitute up to 2 mg of lyophilized, sterile, pharmaceutical grade water-soluble Forskolin analogue, for example water soluble analogue NKH477, in 1 mL of PBS by using a 1 mL syringe. Transfer the reconstituted Forskolin onto the receiving chamber of an intranasal atomizer (NAD nasal) prior to intranasal delivery.

Figure 14:
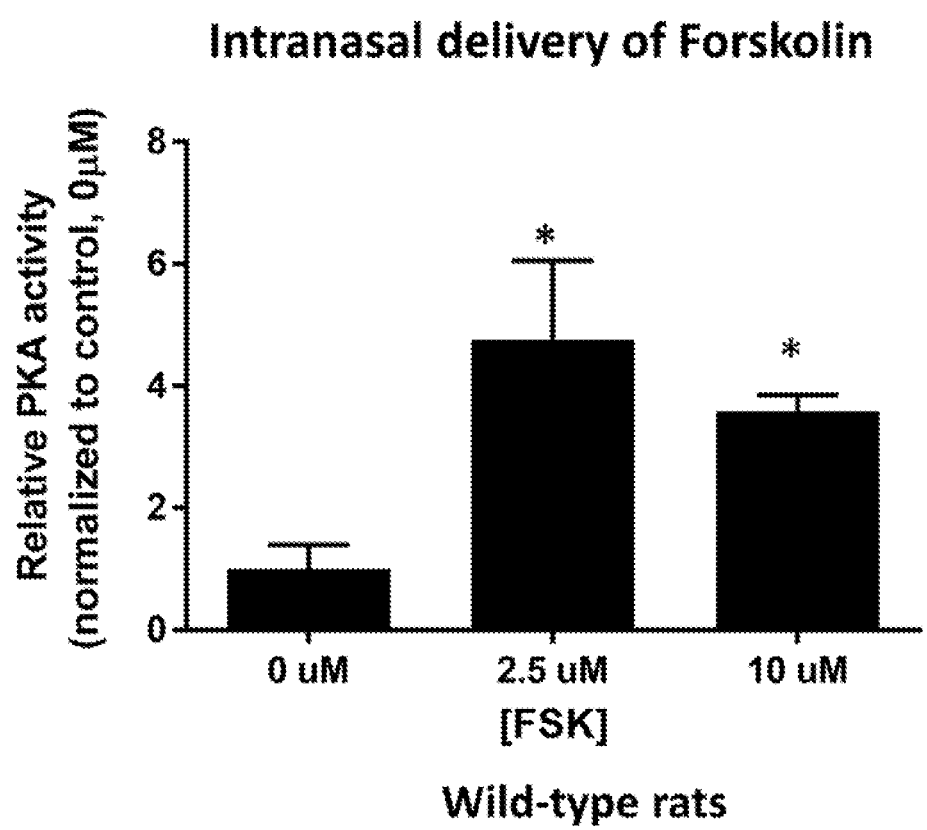
FIG. 14 shows that intranasal administration of Forskolin significantly increases neuroprotective Protein Kinase A (PKA) activity in the cortex of wild-type rats, suggesting that intranasal formulation of Forskolin efficiently crosses the blood brain barrier.

FIG. 14 shows that 24 hr. intranasal administration of Forskolin (6 µl per nostril, pharmaceutical grade Forskolin diluted in PBS at pH 7.4) at the indicated final concentrations (2.5 and 10 µM in cerebrospinal fluid) significantly increases PKA activity in the cortex of wild-type Long-Evans hooded rats. This data shows that intranasal application of Forskolin can efficiently cross the blood brain barrier to increase neuroprotective PKA activity within 24 hrs. of administration. (*:p<0.05 vs. 0 µM, One-Way ANOVA, Tukey's test, N=3 rats per group).

1:1 Ratio of Non-Soluble and Water-Soluble Forms of Forskolin

Combine 1.68 grams $K_2HPO_4$ (60 nM), 5.28 grams $KH_2PO_4$ (40 nM), and 81.8 grams NaCl (1.4 nM). Add distilled $H_2O$ up to 1 L total volume. Autoclave and sterilize solution. Adjust the pH of the solution to 7.4 using a pH meter. Dilute 15 mg of Forskolin in 1.0 mL of DMSO (36.5 mM). Dilute 30 µl of Forskolin/DMSO stock with 0.900 mL of sterile phosphate buffered saline (PBS) containing 15 mg of NKH477. Transfer the formulation onto the receiving chamber of an intranasal atomizer (NAD nasal) prior to intranasal delivery.

Forskolin Formulation with Enhanced Blood-Brain Barrier Penetration

Combine ethyl laurate (1-10% v/v), polysorbate 80 (Tween 80) (1 or 10% v/v), propylene glycol (40% v/v) and ethanol (40% v/v) to form a microemulsion. Reconstitute up to 2 mg of lyophilized, sterile, pharmaceutical grade Forskolin in 1 mL of the microemulsion by using a 1 mL syringe. Transfer the formulation onto the receiving chamber of an intranasal atomizer (NAD nasal) prior to intranasal delivery.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating at least one neurodegenerative disease or disorder in a subject in need thereof, the method comprising administering to the subject:
    a therapeutically effective amount of at least one first compound selected from the group consisting of:

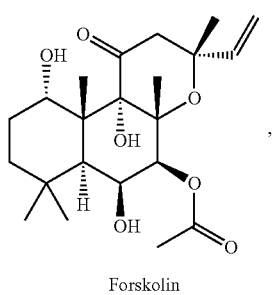

Forskolin

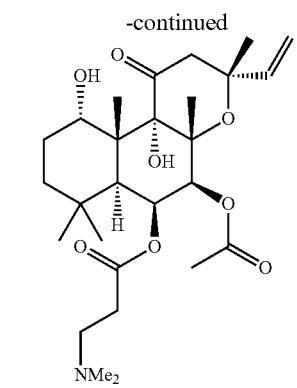

NKH477

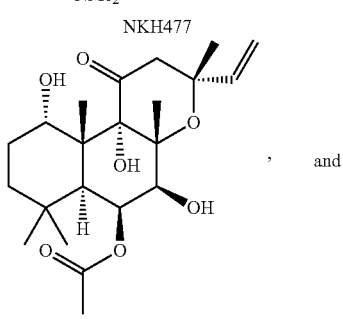

iso-Forskolin

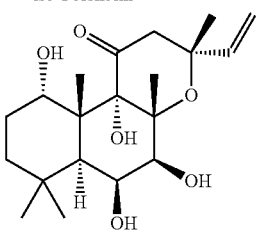

deacetyl-Forskolin, or a salt, isomer, prodrug or solvate thereof; and
    a therapeutically effective amount of at least one second compound selected from the group consisting of Noopept, piracetam, oxiracetam, aniracetam, and pramiracetam, or a salt, prodrug or solvate thereof;
    wherein the at least one neurodegenerative disease or disorder is one selected from the group consisting of Parkinson's disease (PD), Lewy Body Dementia (LBD), Alzheimer's disease, and frontotemporal dementia.

2. The method of claim 1, wherein the therapeutically effective amount of the at least one first compound is administered to the subject intranasally.

3. The method of claim 1, wherein the therapeutically effective amount of the at least one first compound is administered to the subject at least once per day, at least once every two days, at least once every three days, at least once per week or any frequencies and intervals there between.

4. The method of claim 1, wherein the therapeutically effective amount of the at least one first compound is administered to the subject intranasally at least once per day to each nostril.

5. The method of claim 1, wherein the therapeutically effective amount of the at least one first compound is about 0.1 mg/kg to about 10 mg/kg (first compound weight/subject body weight).

6. The method of claim 1, wherein the therapeutically effective amount of the at least one first compound is about 0.1 mg to about 100 mg.

7. The method of claim 1, wherein the therapeutically effective amount of the at least one first compound is administered as part of a pharmaceutical composition further comprising at least one pharmaceutically acceptable carrier.

8. The method of claim 7, wherein the therapeutically effective amount of the at least one first compound is administered as part of an aerosolizable pharmaceutical composition.

9. The method of claim 7, wherein the pharmaceutical composition comprises a total concentration of about 0.1 µM to about 20 µM of the at least one first compound.

10. The method of claim 7, wherein the pharmaceutical composition comprises at least one pharmaceutically acceptable solvent selected from the group consisting of a buffered aqueous solution, a buffered saline solution, ethanol, water, propylene glycol, polyethylene glycol (PEG), glycofurol, dimethylsulfoxide (DMSO) and (4-(2-hydroxyethyl)-1-piperazineethanesulfonic acid) (HEPES).

11. The method of claim 7, wherein the pharmaceutical composition further comprises at least one additional component selected from the group consisting of a pharmaceutically acceptable salt, an emulsifying agent, a flavorant, a scenting agent, a stabilizer, a preservative, and a chelating agent.

12. The method of claim 7, wherein the pharmaceutical composition is a buffered pharmaceutical composition.

13. The method of claim 1, wherein the therapeutically effective amount of the at least one second compound is administered to the subject orally.

14. The method of claim 1, wherein the therapeutically effective amount of the at least one second compound is about 0.01 mg/kg to about 5 mg/kg (second compound weight/subject body weight).

15. The method of claim 1, wherein the therapeutically effective amount of the at least one second compound is about 5 mg to about 50 mg.

16. The method of claim 1, wherein the therapeutically effective amount of the at least one second compound is administered to the subject after the at least one first compound is administered to the subject.

17. The method of claim 16, wherein the at least one first compound is administered intranasally for about 5 days to about 14 days before beginning administration of the therapeutically effective amount of the at least one second compound.

18. The method of claim 1, further comprising administering to the subject at least one additional agent for the treatment of the at least one neurodegenerative disease or disorder.

19. The method of claim 18, wherein the at least one neurodegenerative disease or disorder is Parkinson's disease, and wherein the at least one additional agent for the treatment of Parkinson's disease is selected from the group consisting of cyclic AMP, levodopa (L-dopa), cabidopa, ropinirole, pramipexole, rotigotine, amantadine, trihexyphenidyl, benztropine, selegiline, rasagiline, tolcapone, entacapone, pergolide, ropinirole, phenylzine, tranylcypromine, isocarboxazid, entacapone, and artane.

20. The method of claim 1, wherein the method promotes dendritogenesis and/or neurogenesis in the brain of the subject.

21. The method of claim 20, wherein the method reverses loss of coordination and balance in the subject.

22. The method of claim 20, wherein the method reverses loss of muscular strength in the subject.

23. The method of claim 20, wherein the method reverses loss of oxidative phosphorylation in midbrain of the subject.

24. The method of claim 20, wherein the method reverses loss of dopamine neurons in midbrain of the subject.

25. The method of claim 1, wherein the subject is a mammal.

26. The method of claim 1, wherein the subject is a human.

27. A kit for treating at least one neurodegenerative disease or disorder in a subject in need thereof, the kit comprising:
a pharmaceutical composition comprising at least one first compound selected from the group consisting of:

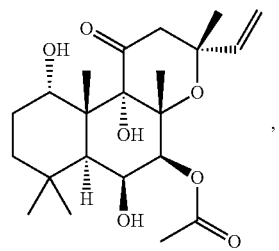

Forskolin

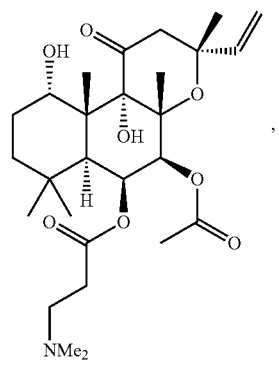

NKH477

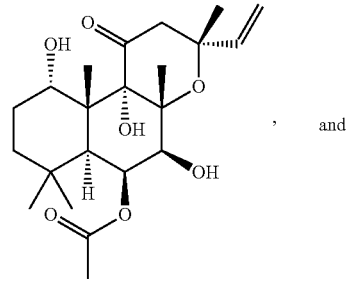

, and iso-Forskolin

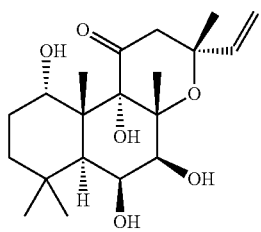

deacetyl-Forskolin, or a salt, isomer, prodrug or solvate thereof;
a pharmaceutical composition comprising at least one second compound selected from the group consisting of Noopept, piracetam, oxiracetam, aniracetam, and pramiracetam, or a salt, prodrug or solvate thereof; and instructional materials detailing methods of treating the at least one neurodegenerative disease or disorder using the pharmaceutical compositions of the kit, wherein the at least one neurodegenerative disease or disorder is one selected from the group consisting of Parkinson's disease (PD), Lewy Body Dementia (LBD), Alzheimer's disease, and frontotemporal dementia.

28. The kit of claim 27, further comprising an applicator for the intranasal administration of the pharmaceutical composition comprising the at least one first compound to the subject.

* * * * *